United States Patent [19]

Emig et al.

[11] Patent Number: 4,738,983
[45] Date of Patent: Apr. 19, 1988

[54] ETHYLENEDIAMINE AND GUANIDINE-DERIVATIVES

[75] Inventors: Peter Emig, Niederdorfelden; Gerhard Scheffler; Klaus Thiemer, both of Hanau; Carl-Heinrich Weischer, Bonn, all of Fed. Rep. of Germany

[73] Assignee: Degussa aktiengesellschaft, Frankfurt, Main, Fed. Rep. of Germany

[21] Appl. No.: 558,984

[22] Filed: Dec. 7, 1983

[30] Foreign Application Priority Data

Dec. 8, 1982 [DE] Fed. Rep. of Germany ....... 3245387

[51] Int. Cl.$^4$ ..................... A61K 31/34; C07D 307/02
[52] U.S. Cl. .................................... 514/471; 549/495
[58] Field of Search ...................... 549/75, 60, 65, 74, 549/76, 479, 492, 493, 494, 495, 496; 424/275, 285; 514/471

[56] References Cited

U.S. PATENT DOCUMENTS

| 4,128,658 | 12/1978 | Price . | |
|---|---|---|---|
| 4,239,769 | 12/1980 | Price et al. | 549/75 |
| 4,252,819 | 2/1981 | Hirata et al. | 549/75 |
| 4,304,780 | 12/1981 | Smith et al. | 549/75 |
| 4,382,929 | 5/1983 | Bradshaw et al. | 549/75 |

FOREIGN PATENT DOCUMENTS

| 36716 | 9/1961 | European Pat. Off. . |
| 2211454 | 10/1972 | Fed. Rep. of Germany . |
| 2344779 | 3/1974 | Fed. Rep. of Germany . |
| 2344833 | 3/1974 | Fed. Rep. of Germany . |
| 2734070 | 2/1978 | Fed. Rep. of Germany . |
| 3100364 | 11/1981 | Fed. Rep. of Germany . |
| 3017628 | 4/1982 | Fed. Rep. of Germany . |

OTHER PUBLICATIONS

Ghosh et al., Brit. J. Pharmacol, (1958), vol. 13, pp. 54-61.
Fieser, Reagents for Organic Synthesis, vol. 1, (1967), pp. 1303-1304.
Fieser, Reagents for Organic Synthesis, vol. 2, p. 471.
Holdren, J. Amer. Chem. Soc., vol. 69, pp. 464-465, (1947).
Gill, J. Chem. Society, (London), pp. 4728-4731, (1958).
Freund, Berichte, vol. 52, pp. 542-544, (1919).
Chem. Berichte, vol. 100, pp. 591-604 and 2604-2615, (1961).

Primary Examiner—Alan Siegel
Attorney, Agent, or Firm—Cushman, Darby and Cushman

[57] ABSTRACT

This invention relates to new compounds corresponding to the general formula:

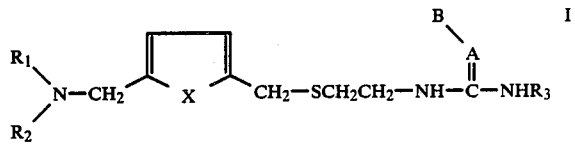

$R_1$ represents a $C_3$-$C_{10}$ cycloalkyl group substituted by $C_1$-$C_6$ alkyl radicals, a $C_3$-$C_{19}$-cycloalkyl-$C_1$-$C_4$ alkyl group which may be substituted by $C_1$-$C_6$ alkyl radicals, a $C_6$-$C_8$ bicycloalkyl group, a $C_6$-$C_8$ bicycloalkyl-$C_1$-$C_4$ alkyl group, a $C_6$-$C_{10}$ tricycloalkyl group, a $C_6$-$C_{10}$ tricycloalkyl-$C_1$-$C_4$ alkyl group, a $C_6$-$C_9$ tetracycloalkyl group or a $C_6$-$C_9$-tetracycloalkyl-$C_1$-$C_4$ alkyl group, $R_2$ represents hydrogen, a $C_1$-$C_6$ alkyl group, a phenyl-$C_1$-$C_4$ alkyl group or a $C_1$-$C_6$ alkyl group which is substituted by halogen atoms, nitro groups, hydroxy groups, $C_2$-$C_6$ alkanoyloxy groups, $C_1$-$C_4$ alkoxy groups, $C_1$-$C_4$ alkoxy carbonyl groups or carboxy groups, $R_3$ represented hydrogen, the 2-[5-(dimethylaminomethyl)-2-furyl-methylthio]-ethyl group, a $C_1$-$C_{18}$-alkyl group, a $C_3$-$C_6$-cycloalkyl group, a $C_3$-$C_6$-alkenyl group, a $C_3$-$C_6$-alkinyl group, an amino-$C_1$-$C_4$-alkyl group, a $C_2$-$C_6$-alkanoylamino-$C_1$-$C_4$-alkyl group, a mono-$C_1$-$C_6$-alkylamino-$C_1$-$C_4$-alkyl group, a di-$C_1$-$C_6$-alkylamino-$C_1$-$C_4$-alkyl group or a $C_1$-$C_{18}$-alkyl group, which is substituted by halogen atoms, nitro groups, hydroxy groups, $C_2$-$C_6$ alkanoyloxy groups, $C_1$-$C_4$ alkoxy groups, $C_1$-$C_4$ alkoxycarbonyl groups or carboxy groups, A represents a nitrogen atom or a methine group,
B represents a cyano radical or a nitro group, and
X represents an oxygen atom or a sulphur atom, and salts thereof.

The compounds inhibit the secretion of gastric juice. Moreover, they have an ulcer-inhibiting and stomach-spasmolytic effect.

19 Claims, No Drawings

ETHYLENEDIAMINE AND GUANIDINE-DERIVATIVES

BACKGROUND OF THE INVENTION

Compounds which correspond to the following general formula are known (see German Offenlegungsschrift No. 2,344,833):

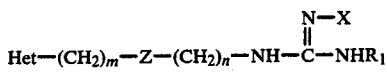

$$\text{Het}-(CH_2)_m-Z-(CH_2)_n-NH-\overset{\overset{N-X}{\|}}{C}-NHR_1$$

wherein $R_1$ represents a hydrogen atom or an alkyl radical having from 1 to 4 carbon atoms, Het represents a nitrogen-containing 5- or 6-membered heterocyclic radical Z represents a sulphur atom or an oxygen atom, an NH- or methylene group, m and n represent the value 0 or integers from 1 to 4, and the total of m and n is from 2 to 4, X represents a $COR_3-$, $CSR_3-$, $SO_2R_4-$ OR $-N=CHR_5$ group, or if Z represents a methylene group, X represents a nitro group, $R_3$ represents an alkyl or alkoxy radical having from 1 to 4 carbon atoms, an optionally substituted aryl radical, a trifluoromethyl or amino group, and $R_4$ and $R_5$ represent an optionally substituted aryl radical, and salts thereof. The entire disclosure of German OS No. 2,344,833 is hereby incorporated by reference and relied upon.

Furthermore, German Offenlegungsschrift No. 2,734,070 discloses aminoalkylfuran derivatives corresponding to the general formula

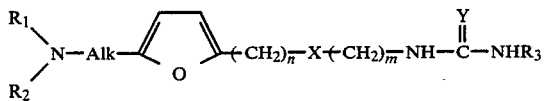

and salts and N-oxides thereof, wherein $R_1$ and $R_2$ which may be the same or different, represent hydrogen, lower alkyl, cycloalkyl, lower alkenyl, aralkyl or lower alkyl which is interrupted by an oxygen atom or a group

wherein $R_4$ represents hydrogen or lower alkyl, or wherein $R_1$ and $R_2$, together with the nitrogen atom to which they are joined, may form a heterocyclic ring which may contain O and/or

as heteroatoms, wherein furthermore $R_3$ represents hydrogen, lower alkyl, lower alkenyl or alkoxyalkyl, X represents $-CH_2-$, O or S, Y represents $=S$, $=O$, $=NR_5$ or $CHR_6$, Alk represents a straight or branched alkylene chain having from 1 to 6 carbon atoms, $R_5$ represents H, nitro, cyano, lower alkyl, aryl, alkylsulphonyl, or a;rylsulphonyl, $R_6$ represents nitro, arylsulphonyl or alkylsulphonyl, m represents an integer from 2 to 4 and n represents 1 or 2, or if X represents sulphur or $-CH_2-$, n represents 0, 1 or 2. The entire disclosure of German OS No. 2,734,070 is also hereby incorporated by reference and relied upon.

An antihistamine effect of the $H_2$-blocker type is specified for these previously known compounds. They prevent the secretion of gastric juice when this is stimulated by histamine-$H_2$ receptors. However, the activity of these known compounds is only relatively low, but in particular it is only brief.

SUMMARY OF THE INVENTION

The invention is directed to compounds corresponding to the general formula

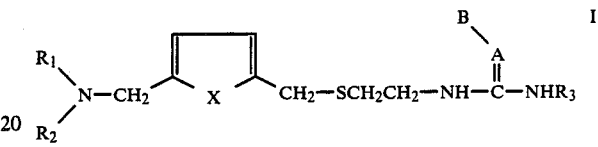

wherein $R_1$ represents a $C_3$-$C_{10}$ cycloalkyl group (e.g. cyclopropyl, cyclopentyl, cyclohexyl, cyclooctyl, cyclodecyl) substituted by $C_1$-$C_6$ alkyl radicals (e.g. methyl, ethyl, butyl, hexyl, sec. butyl, isopropyl), a $C_3$-$C_{10}$-cycloalkyl-$C_1$-$C_4$-alkyl group (e.g. cyclohexylmethyl, cyclohexylbutyl) which may be substituted by $C_1$-$C_6$-alkyl radicals, a $C_6$-$C_8$ bicycloalkyl group, a $C_6$-$C_8$-bicycloalkyl-$C_1$-$C_4$ alkyl group, a $C_6$-$C_{10}$-tricycloalkyl group, a $C_6$-$C_{10}$-tricycloalkyl-$C_1$-$C_4$ alkyl group, a $C_6$-$C_9$-tetracycloalkyl group or a $C_6$-$C_9$-tetracycloalkyl-$C_1$-$C_4$ alkyl group, $R_2$ represents hydrogen, a $C_1$-$C_6$ alkyl group, a phenyl-$C_1$-$C_4$-alkyl group (e.g. phenylmethyl, phenylethyl, phenylbutyl) or a $C_1$-$C_6$ alkyl group which is substituted by halogen atoms (e.g. chloromethyl, bromoethyl, fluoromethyl, trifluoromethyl, chlorohexyl), nitro groups, hydroxy groups, $C_2$-$C_6$-alkanoyloxy groups (e.g. acetoxy, propionoxy, hexanoyloxy), $C_1$-$C_4$-alkoxy groups (e.g. methoxy, ethoxy, butoxy), $C_1$-$C_4$ alkoxy carbonyl groups (e.g. methoxycarbonyl, butoxycarbonyl) or carboxy groups, $R_3$ represents hydrogen, the 2-[5-(dimethylaminomethyl)-2-furyl-methylthio]-ethyl group, a $C_1$-$C_{18}$-alkyl-group (e.g. methyl, ethyl, isopropyl, butyl, decyl, octadecyl), a $C_3$-$C_6$-cycloalkyl group (e.g. cyclopropyl, cyclopentyl, cyclohexyl), a $C_3$-$C_6$-alkenyl group (e.g. allyl, methallyl, crotyl), a $C_3$-$C_6$-alkinyl group (e.g. methylethinyl), an amino-$C_1$-$C_4$-alkyl group (e.g. aminomethyl, aminoethyl, aminobutyl), a $C_2$-$C_6$-alkanoylamino-$C_1$-$C_4$-alkyl group (e.g. acetaminoethyl, acetaminobutyl), a mono-$C_1$-$C_6$-alkylamino-$C_1$-$C_4$-alkyl group (e.g. methylaminoethyl, ethylaminomethyl, hexylaminoethyl), a di-$C_1$-$C_6$-alkylamino-$C_1$-$C_4$-alkyl group (e.g. dimethylaminoethyl) or a $C_1$-$C_{18}$-alkyl group, which is substituted by halogen atoms (e.g. chloromethyl, chlorooctadecyl, bromoethyl, trifluoromethyl), nitro groups, hydroxy groups, $C_2$-$C_6$ alkanoyloxy groups (e.g. acetoxy, propionoxy), $C_1$-$C_4$ alkoxy groups (e.g. methoxy, ethoxy), $C_1$-$C_4$ alkoxycarbonyl groups (e.g. methoxycarbonyl) or carboxy groups, A represents a nitrogen atom or a methine group, B represents a cyano radical or a nitro group, and X represents an oxygen atom or a sulphur atom and salts thereof, e.g. pharmaceutically acceptable salts, e.g. salts of sulfuric acid, hydrochloric acid, succinic acid.

The invention also is directed to a process for the production of compounds $$\underset{R_2}{\overset{R_1}{\diagdown}}N-CH_2-\underset{X}{\boxed{\phantom{xx}}}-CH_2-SCH_2CH_2-NH-\underset{\overset{\|}{A}}{\overset{B}{\diagdown}}C-NHR_3 \qquad I$$

comprising reacting (a) a compound corresponding to the formula $$T-\underset{\overset{\|}{A}}{\overset{B}{\diagdown}}C-Y-\text{alkyl} \qquad II$$

wherein
Y represents a sulphur atom or an oxygen atom,
A and B are as defined above, and
alkyl represents a saturated $C_1$–$C_6$ alkyl radical with a compound corresponding to the formula $$H-V \qquad III$$

and T and V in the formulae II and III are different in each case and either represent the group $$\underset{R_2}{\overset{R_1}{\diagdown}}N-CH_2-\underset{X}{\boxed{\phantom{xx}}}-CH_2-SCH_2CH_2-NH-$$

or the group —$NHR_3$, and $R_1$, $R_2$, $R_3$ and X are as defined above, or reacting (b) a compound corresponding to the formula $$Z-(CH_2)_2-NH-\underset{\overset{\|}{A}}{\overset{B}{\diagdown}}C-NHR_3 \qquad IV$$

with a compound corresponding to the formula $$\underset{R_2}{\overset{R_1}{\diagdown}}N-CH_2-\underset{X}{\boxed{\phantom{xx}}}-CH_2U \qquad V$$

and $R_1$, $R_2$, $R_3$, X, B and A in the formulae IV and V are as defined above, and Z and U are different in each case, and either represent a mercapto group or a hydroxy group which may also be esterified by a strong organic or inorganic acid, or introducing (c) the radical $R_1$ and/or the radical $R_2$ into a compound corresponding to the formula $$HRN-CH_2-\underset{X}{\boxed{\phantom{xx}}}-CH_2-S-CH_2-NH-\underset{\overset{\|}{A}}{\overset{B}{\diagdown}}C-NHR_3 \qquad VI$$

wherein R represents hydrogen, the radical $R_1$ or the radical $R_2$, and the radicals $R_1$ and $R_2$ are as defined above, apart from hydrogen for $R_2$, and/or a group which corresponds to the definition of $R_3$, excluding hydrogen into a compound corresponding to formula VI, wherein $R_3$ represents hydrogen, or introducing (d) the group $R_1R_2NCH_2$ into a compound of the formula $$\underset{X}{\boxed{\phantom{xx}}}-CH_2-S-CH_2NH-\underset{\overset{\|}{A}}{\overset{B}{\diagdown}}C-NHR_2 \qquad VII$$

by reacting with a bis-amine corresponding to the formula $$(R_1R_2N)_2CH_2 \qquad VIII$$

or with an amine $R_1R_2NH$ in the presence of formaldehyde or in the presence of a formaldehyde-producing substance and the compounds which are obtained are optionally acylated and/or converted into a salt.

The compounds according to the present invention have a pharmacological activity. For example, they inhibit the secretion of stomach acid, and have a strong antihistamine action of the "$H_2$-blocker" type. In particular, they have a long-lasting effect. Furthermore, they have a specific ulcer-curing or -inhibiting effect. Moreover, they have a specific stomach-spasmolytic effect.

Thus, an object of the present invention is to provide compounds which have favorable pharmacological properties and which may be used as medicaments.

Surprisingly, on the other hand, the compounds according to the present invention have a stronger and longer-lasting effect than the compounds which are already known.

The alkyl, alkenyl, alkinyl, alkoxy, alkylamino, alkanoyl, alkoxy carbonyl and alkylene groups which occur in formula I (for example the $C_1$–$C_4$ alkylene group in the form of the di-$C_1$–$C_6$ alkylamino -$C_1$–$C_4$ alkyl group, the amino-$C_1$–$C_4$ alkyl group, the $C_3$–$C_{10}$ cycloalkyl-$C_1$–$C_4$ alkyl group, the phenyl-$C_1$–$C_4$ alkyl group and similar groups) may be straight or branched. Examples of an alkylene group of this type include the following: —$CH_2$—, —$CH_2$—$CH_2$—, —$(CH_2)_3$—, —$(CH_2)_4$—, $$-\underset{\underset{CH_3}{|}}{CH}-CH_2-, \quad -\underset{\underset{CH_3}{|}}{CH}-(CH_2)_2-, \quad -CH_2\underset{\underset{CH_3}{|}}{CH}-CH_2-.$$

If $R_1$ represents a $C_3$–$C_{10}$ cycloalkyl group or if $R_3$ represents a $C_3$–$C_6$ cycloalkyl group, it is, for example the cyclopropyl, cyclobutyl, cyclopentyl, cyclohexyl, cycloheptyl, cyclooctyl, cyclononyl or cyclodecyl group. The same applies accordingly with respect to the $C_3$–$C_{10}$-cycloalkyl-$C_1$–$C_4$ alkyl group, in which case the alkylene group of the compound consists preferably of 1 or 2 carbon atoms. The latter also applies to all other cases in which an alkylene group which is defined as above is present.

The $C_3$–$C_{10}$ cycloalkyl group may contain 1, 2, 3 or 4 alkyl radicals, and they are preferably methy and isopropyl radicals. Examples include the following: the 1-methyl-4-isopropyl-cyclohexyl-(2)-radical, and the 2-(2,2,3)-trimethyl-cyclopent-1-yl-)-ethyl-radical. Examples of the di-$C_1$–$C_4$-alkylamino-$C_1$–$C_4$-alkyl group are as follows: The β-diethylamino-ethyl group, the β-dimethylaminoethyl group, the α-diethylamino-propyl group, and the α-dimethylaminopropyl group. Examples of the $C_1$–$C_4$-alkoxycarbonyl group are: the methoxy carbonyl group, the ethoxy carbonyl group, the propoxy carbonyl group and the butoxy carbonyl group. Examples of the alkenyl and alkinyl groups are as follows: the allyl group, the prop-1-en-3-yl-group, the but-1-en-4-yl group, the but-2-en-4-yl group, the pent-1-en-5-yl-group and the prop-1-inyl-group. The alkenyl and alkinyl groups consist in particular of 3 or 4 carbon atoms.

The $R_2$ represents an optionally substituted $C_1$–$C_6$ alkyl group or if the $C_1$–$C_6$ alkyl radical is a constituent of a substituent, such an alkyl group or such an alkyl radical preferably consists of from 1 to 4 carbon atoms.

If $R_3$ represents a $C_1$–$C_{18}$ alkyl group, it is in particular a $C_1$–$C_{12}$ alkyl group. Examples of this alkyl group and of the $C_1$–$C_6$ alkyl group are as follows: the methyl, ethyl, propyl, butyl, hexyl, heptyl, octyl, decyl, dodecyl, isopropyl, isobutyl, tert. butyl and isoamyl groups. Examples of the substituted $C_1$–$C_{18}$ alkyl group include the 2-methoxy ethyl, 2-chloroethyl, 2-nitroethyl and 3-chloropropyl groups. In particular, the $C_1$–$C_{18}$ alkyl group is mono-, di- or tri-substituted in the 2- or 3-position by halogen atoms, hydroxy groups, $C_2$–$C_6$ alkanoyloxy groups, nitro groups or $C_1$–$C_4$ alkoxy groups. The same applies if $R_2$ represents the substituted $C_1$–$C_6$ alkyl group. If $R_2$ represents a $C_1$–$C_6$ alkyl group (substituted or unsubstituted), it preferably consists of 1, 2, 3 or 4 carbon atoms. Examples of the $C_1$–$C_4$ alkoxy group include the methoxy, ethoxy, propoxy and butoxy groups.

The alkyl radical in the form of the phenyl-$C_1$–$C_4$-alkyl radical preferably consists of 1 or 2 carbon atoms.

If the radicals $R_1$ and/or $R_3$ contain halogen atoms, they represent fluorine, chlorine, bromine or iodine.

If the radicals $R_2$ and/or $R_3$ contain alkanoyl groups (alkanoyloxy or alkanoylamino), then they are in particular groups which contain from 2 to 4 carbon atoms, for example the acetyl group, the propionyl group or the butyryl group.

An example of the $C_6$–$C_{10}$ tricycloalkyl group is the tricycloheptyl group, for example the tricyclo-(2.2.1.0.$^{2,6}$)hept-3-yl group corresponding to the following structure

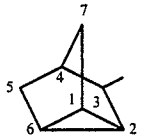

or the tricyclodecyl group (for example the tricyclo(3.3.1.1.$^{3,7}$)dec-1-yl group; the tricyclo(3.3.1.1.$^{3,7}$)dec-2-yl group:

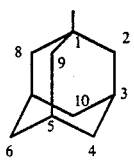

An example of the $C_6$–$C_{10}$ tricycloalkyl-$C_1$–$C_4$ alkyl group is the tricycloheptylmethyl or -ethyl group, for example the tricyclo(2.2.1.0.$^{2,6}$)hept-3-yl-methyl or ethyl group corresponding to the following structure

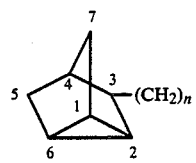

n = 1 or 2 or the tricyclo(3.3.1.1.$^{3,7}$)dec-1(2)-yl-methyl group.

An example of the $C_1$–$C_9$-tetracycloalkyl group is the tetracyclo(4.3.0.0.$^{2,4}$0$^{3,7}$)non-8-yl group

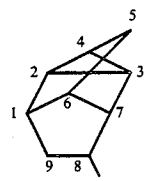

or the tetracyclo(4.3.0.0.$^{2,4}$0$^{3,7}$)non-8-yl-methyl group.

An example of the $C_1$–$C_8$ bicycloalkyl group is the bicycloheptyl group or the bicyclooctyl group, for example the bicyclo(2.2.1.)hept-2-yl group

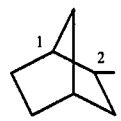

or the bicyclo(2.2.2.)octyl-2 group

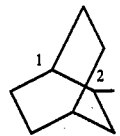

or the bicyclo(2.2.1.)hept-2-yl-methyl group or the bicyclo(2.2.2.)oct-2-yl-methyl group.

In such products corresponding to formula I wherein $R_2$ and/or $R_3$ contain a hydroxy group and/or $R_3$ contains an amino group, these groups may be acylated by a $C_2$–$C_6$ alkanoyl group. Acylation is carried out in a known manner, for example using $C_2$–$C_6$ alkanoyl halides, e.g. acetyl chloride or bromide, or $C_2$–$C_6$ alkanoyl anhydries, e.g. acetic anhydride. For example, acylation is carried out in a solvent or dispersing agent (aliphatic halogenated hydrocarbons, such as chloroform, dichloromethane, lower aliphatic ketones, e.g. acetone, dioxane, dimethylformamide, n-hexane, benzene or toluene) in the presence of an acid-binding substance, (e.g. pyridine, trialkylamines, e.g. triethylamine, alkali carbonates, e.g. sodium carbonate, potassium carbonate, alkali hydroxides, e.g. sodium hydroxide, potassium hydroxide, alkali hydrogen carbonates, e.g. sodium bicarbonate, alkaline earth carbonates, e.g. calcium carbonate, and alkali acetates, e.g. sodium acetate) at a temperature of from 0° to 180° C., preferably from 0° to 100° C.

If appropriate, acylation may also be carried out so that first of all, an alkali compound is produced from the compound which is to be acylated by reacting it with an alkali metal, e.g. sodium, alkali hydride, e.g. sodium hydride, or alkali amides (in particular sodium or sodium compounds) in an inert solvent, such as dioxane, dimethylformamide, benzene or toluene, at a temperature of 0° to 150° C., and the adding the acylating agent.

Instead of using the acylating agents which have been stated, it is also possible to use chemically equivalent agents which are conventional in chemistry (see, for example: L. F. and Mary Fieser "Reagents for Organic Synthesis", John Wiley and Sons, Inc., New York, 1967, Vol. 1, page 1303–4 and Vol. 2, page 471).

For process (a):

The process is carried out, for example in a solvent at a temperature of from −20° to +200° C., preferably from 10° to 150° C. Bases (for example alkali carbonates) may optionally also be added. In the case of volatile amines, the process must be carried out in a closed system, and optionally under pressure (for example up to 100 bars).

The following are included as solvents: polar solvents, such as water or alcohols (methanol, ethanol, n-propanol, iso-propanol or butanol), straight-chain ethers, such as dimethyl ether, diethyl ether or glycol dimethyl ether, cyclic ethers, such as tetrahydrofuran or dioxane, lower ketones, such as acetone, also dipolar aprotic solvents, such as dimethylformamide, dimethylacetamide, dimethylsulphoxide, hexamethylphosphoric acid triamide or sulpholane, also acetonitrile or aromatic solvents, such as benzene, toluene or xylene, and excess amine.

It is also possible to use mixtures of the above-mentioned solvents, for example mixtures of toluene and water or mixtures of xylene and water.

In the process, a compound in which Y represents a sulphur atom is preferably used as starting compound II. If the group >AB represents, for example the group =N—CN, materials in which T represents the group —NHR₃ and Y represents oxygen are particularly also suitable as starting materials corresponding to formula II.

The starting materials for this process, which are not known, may be produced for example analogously to the processes which are described in German Offenlegungsschrift Nos. 2,344,833; 2,734,070; 2,211,454 and 2,344,779. The entire disclosures of all of these publications are hereby incorporated by reference and relied upon.

Starting materials corresponding to formula II, wherein Y represents an oxygen atom and T represents the group —NHR₃ may be obtained, for example analogously to Chemische Ber. 100, pages 2604–2615 (1967), in particular page 2607 or 2609. The entire disclosure of this article is hereby incorporated by reference and relied upon. The starting materials corresponding to formula II, wherein Y represents oxygen and T represents the other amine part with the thiophene or furan radical may also be obtained in the same way by reacting, for example compounds $(C_2H_5O)_2C=A—B$ (=A—B, for example =N—CN) with an amine corresponding to the formula $R_1R_2N—CH_2—Het—CH_2—S—CH_2—CH_2—NH_2$ (Het = furan or thiophene radical).

Starting materials corresponding to formula II, wherein T represents the group

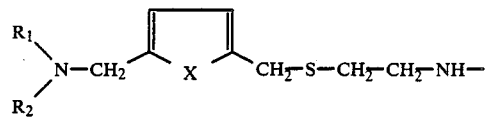

may be obtained, for example as described in the following.

An amino compound corresponding to the formula $R_1R_2NH$ (in the form of the salt thereof, for example as hydrochloride) is reacted with 2-furylmethanol or 2-thienyl-methanol in a solvent (lower alcohols, such as methanol or ethanol; aliphatic ethers, such as dimethylether or diethylether; aromatic hydrocarbons, such as benzene or toluene) in the presence of formaldehyde or a formaldehyde-producing substance (paraformaldehyde, trioxane) at from 0° to 120° ° C., preferably from 30° to 80° C., and the hydroxy methyl intermediate stage corresponding to the following formula is obtained:

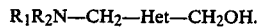

In this formula, Het represents a furan or thiophene radical which is joined to the substituents in each case in the 2- and 5-position. (See J. Am. Chem. Soc. 69 (1947), page 464; J. Chem. Soc. (1958), page 4728). The entire disclosures of these articles are hereby incorporated by reference and relied upon.

However, this intermediate stage may also be produced analogously to European application No. 36 716 using a bis-amine corresponding to the formula $(R_1R_2N)_2CH_2$. It is possible to produce the mercapto compund $R_1R_2N—CH_2—Het—CH_2SH$ from the corresponding compound $R_1R_2N—CH_2—Het—CH_2OH$ by the process which is stated in German Offenlegungsschrift No. 3,100,364 on pages 6 and 7. The entire disclosures of European application No. 36 716 and German OS No. 3,100,364 are hereby incorporated by reference and relied upon.

If $R_2$ represent hydrogen in the above-mentioned intermediate stage, the radical $R_2$ (having one of the specified meanings, apart from hydrogen) may be introduced by conventional alkylation, for example by a reaction with a compound $R_2Hal$, wherein Hal represents chlorine, bromine or iodine.

An intermediate compound as stated above may also be produced analogously, in which compound $R_1$ represents hydrogen ($R_2$ may assume the specified meanings, including hydrogen). In this case, the radical $R_1$ (having the appropriate meanings) must then be compulsorily introduced by conventional alkylation, for example by a reaction with a compound $R_1Hal$, wherein Hal represents chlorine, bromine or iodine, and $R_1$ assumes the specified meanings, excluding hydrogen.

The alkylation reaction is optionally carried out with the addition of conventional acid-binding agents, such as alkali hydroxides, alkali carbonates or alkali hydrides at a temperature of from 0° to 150° C. in inert solvents, such as dioxane, dimethylformamide, dimethylsulphoxide, aromatic hydrocarbons (such as benzene or toluene) or in acetone.

Alkylation may also be carried out in the presence of tetraalkylammonium salts (in particular the halides) combined with alkali hydroxides at a temperature of from 0° to 100° C., preferably from 20° to 80° C. in an aprotic solvent or in chloroform or methylene chloride. The following are included as examples of aprotic solvents: tertiary amides (dimethylformamide, N-methylpyrrolidone, hexamethylphosphoric acid amide), dimethylsulphoxide,, acetonitrile, dimethoxy ethane, acetone and tetrahydrofuran.

If appropriate, alkylation may also be carried out such that first of all an alkali compound is produced from the compound to be alkylated by reacting it with an alkali metal, alkali hydride or alkali amides (in particular sodium or sodium compounds) in an inert solvent, such as dioxane, dimethylformamide, benzene or toluene, at a temperature of from 0° to 150° C. and then adding the alkylating agent.

It is then possible to obtain the amines corresponding to the formula $R_1R_2N-CH_2-Het-CH_2-S-(CH_2)_2-NH_2$ from the above-mentioned hydroxy methyl or mercaptomethyl intermediate stage, for example according to German Offenlegungsschrift No. 2,734,070, pages 25 to 33. In the case of the corresponding thiophene compounds, the process is carried out analogously to the production of the corresponding furan compounds only by using the corresponding thiophene derivatives instead of the furan starting compounds.

Such starting amines may also be obtained, for example by reacting compounds corresponding to the formula $R_1R_2N-CH_2-Het-CH_2-Q$, wherein Q represents an hydroxyl or a methoxy group or a halogen atom (Het may be defined as stated above) with an 1-aminomercaptan corresponding to the formula $HS-(CH_2)_2-NH_2$ under the conditions stated in German Offenlegungsschrift No. 2,406,166 (pages 8 to 9), in British Pat. No. 1,338,169 (the entire disclosures of German OS No. 2,406,166 and British Pat. No. 1,338,169 are hereby incorporated by reference and relied upon) and in German Offenlegungsschrift No. 2,734,070, pages 23 to 27. If Q represents a halogen atom, this reaction may be carried out in a strongly alkaline medium, for example in the presence of sodium ethoxide, potassium hydroxide, sodium hydroxide, tertiary amines (triethyl amine) or strongly basic ion exchangers. It may be necessary to protect the amino group of the ω-aminomercaptan starting compound, for example by converting it into a phthalimide group which is subsequently split off again by acid hydrolysis or hydrazinolysis. If appropriate, the reaction may also take place in an acid medium, for example in the presence of a hydrohalic acid, such as 48% aqueous hydrobromic acid or in a hydrohalic acid in the presence of glacial acetic acid, or in glacial acetic acid (reflux), if Q represent an hydroxyl group.

If Q represents a methoxy group, the reaction may also take place in the presence of 48% hydrobromic acid.

Furthermore, starting amines corresponding to the formula $R_1R_2N-CH_2-Het-CH_2-S-(CH_2)_2-NH_2$ may be obtained from the above-mentioned hydroxy methyl intermediate stage $R_1R_2N-CH_2-Het-CH_2-OH$ according to or analogously to the method stated in German Offenlegungsschrift No. 3,107,628 on pages 43 to 45. For the production of the hydroxy methyl intermediate stage, it is also possible to refer to, for example the information in German Offenlegungsschrift No. 3,107,628, page 44, paragraph 3.

The group $-C(=AB)-S-$alkyl is introduced into the amines corresponding to the formula $R_1R_2N-CH_2-Het-CH_2-S-(CH_2)_2-NH_2$ (for example by a reaction with $(CH_3S)_2-CHNO_2$ or $(CH_3S)_2C=N-CN$ analogously to Chem. Ber. Vol. 52 (1919), page 542 or Vol. 100 (1967), page 591). The entire disclosures of both of the articles are hereby incorporated by reference and relied upon. Furthermore, this method of production is described in, among other publications, German Offenlegungsschrift No. 2,734,070 (see in particular pages 21 and 22) or it is carried out analogously thereto.

The starting amines $R_1R_2NH$ are known or they may be produced, for example by or analogously to, the method described in the following.

A starting amine $NH_2R_1$ wherein $R_1$ represents the tetracyclo(4.3.0.0.$^{2.4}$0$^{3.7}$) non-8-yl group (see page 11) may be obtained, for example from tetracyclo(4.3.0.0.$^{2.4}$0$^{3.7}$) nonan-8-one by a reaction with ammonia in methanol or isopropanol at from 20° to 50° C. in the presence of hydrogen and Raney nickel (as catalyst) under a pressure of from 1 to 30 bars and by a subsequent acid-alkaline treatment of the reaction product.

The amine is appropriately isolated as hydrochloride.

A starting amine $NH_2R_1$, wherein $R_1$ represents the bicyclo(2.2.2.)octyl-2-group (see page 12, line 1) may be produced, for example from bicyclo(2.2.2.)oct-(5)-en-one-(2) in the same way as before. 2-amino-adamantane, for example may be produced analogously from 2-oxo-adamantane.

Starting amines $NH_2R_1$, wherein $R_1$ represents a $C_6-C_8$ bicycloalkyl methyl group, a $C_3-C_{10}$ tricycloalkyl methyl group or a $C_6-C_9$ tetracycloalkyl methyl group may be obtained, for example by reducing the corresponding polycyclic cyanides using lithium aluminium hydride in tetrahydrofuran with ice cooling. Thus, for example bicyclo(2.2.1.)hept-2-yl-methylamine may be produced from the known bicyclo(2.2.1.) hept-2-yl-cyanide as follows.

A suspension of 12 g of lithium aluminium hydride in 200 ml of anhydrous tetrahydrofuran is mixed dropwise under a nitrogen atmosphere and while cooling with ice, with a solution of 10 g of bicyclo(2.2.1.)-hept-2-yl-cyanide in 50 ml of anhydrous tetrahydrofuran. After stirring for 4 hours while cooling with ice, the temperature of the reaction mixture is allowed to rise to 25° C. with further stirring and the mixture is then heated for 2 hours at 40° C. After cooling to room temperature, the mixture is slowly mixed with water, the precipitating inorganic proportion is filtered and the filtrate is dried over anhydrous sodium sulphate. The operations of filtration and concentration of the filtrate under vacuum at room temperature produce the "amine" in a form which is homogeneous according to thin layer chromatography. Yield: 82–87% of the theoretical yield.

Tetracyclo(4.3.0.0.$^{2.4}$0$^{3.7}$)non-8-yl-cyanide, tricyclo(3.3.1.1.$^{3.7}$)dec-1(2)-yl-cyanide and tricyclo(2.2.1.0.$^{2.6}$)hept-3-yl-cyanide, for example may be reduced anlogously into the corresponding amines. Bicyclo(2.2.2.)oct-2-yl-methylamine may be obtained, for example from the known bicyclo(2.2.2.)-oct-5-en-2-yl-cyanide by hydrogenation in methanol or isopropanol at from 20° to 50° C. and under 1 to 50 bars in the presence of palladium.

Tricyclo-(2.2.1.0$^{2.6}$)hept-3-yl-cyanide may be obtained, for example from 2-chloro-norborn-5-ene as follows.

1 mol (24.3 g) of iodine-activated magnesium is coated with dry ether and slowly mixed dropwise with a solution of 1 mol (128.5 g) of 2-chloro-norborn-5-ene in 400 ml of dry ether, so that the reaction takes place with gentle boiling. (The dropwise addition lasts for about 3 hours.) Thereafter, the mixture is stirred for 1 hour at boiling temperature. After the mixture has cooled, it is added with constant stirring to a considerable excess of solid $CO_2$ in about 300 ml of dry ether (very vigorous reaction). Once the reaction has subsided, the reaction product is crushed and is added to a mixture of a large amount of ice and 100 g of concentrated $H_2SO_4$ (98%), and is extracted with ether. The resulting tricyclo(2.2.1.0.$^{2\cdot6}$)hept-3-yl-carboxylic acid is worked up in an alkaline-acid manner for purification purposes. The organic phases are dried over $Na_2SO_4$ and then concentrated under vacuum and fractionated: b.p. $_{(10)}$ 130° to 135° C. The substance crystallises out: m.p. 46°–47° C. Yield: 67% of the theoretical yield. $R_f$ value: 0.294 at 23° C. (eluant: chloroform:methanol 25:1; dyeing reagent: iodine; adsorbent: silica gel; quantity applied: 250 q).

A homogeneous mixture of 32.7 g (0.237 mols) of tricyclo(2.2.1.0$^{2\cdot6}$)-hept-3-yl-carboxylic acid, 21.3 g (0.355 mols) of urea and 46 g (0.474 mols) of amidosulphuric acid is rapidly heated to from 250° to 270° C. by means of a metal bath in a round-bottomed flask having a descending Liebig condenser and two cooling traps (cooled in acetone-dry ice). A melt is produced for a short time which then foams up and solidifies after 10 to 20 minutes (strong decomposition fumes). Thereafter, the end product distils off within half an hour under a water jet vacuum (b.p. about 80°–130° C.). The crude product obtained in this manner is dissolved in ether and toluene, dried over some $Na_2SO_4$, concentrated on a rotary evaporator and fractionated in a water jet vacuum:

b.p. $_{(10)}$:
80°–83° C. fore-run
84°–86° C. main fraction
Yield: about 85% of the theoretical yield.

The amines $NR_1R_2H$ may be obtained from amines corresponding to the formula $NH_1H_2$, for example by introducing the radical $R_2$ ($R_2$ is defined as stated above) into an amine corresponding to the formula $NR_1H_2$ by conventional alkylation. Alkylation may be carried out, for example by a reaction with compounds $HalR_2$, Hal representing chlorine, bromine or iodine, and $R_2$ representing a $C_1$–$C_6$ alkyl group or a phenyl $C_1$–$C_4$ alkyl group, or a $C_1$–$C_6$ alkyl group which is substituted by halogen atoms, nitro groups, hydroxy groups, $C_6$–$C_6$ alkanoyloxy groups, $C_1$–$C_4$ alkoxy groups, $C_1$–$C_4$ alkoxy carbonyl groups or carboxy groups. Conversely, an amine corresponding to the formula $NR_1R_2H$ may be obtained, for example by reacting an amine $NR_2H_2$ with a compound $R_1Hal$ ($R_1$ is as defined above and Hal represents chlorine, bromine or iodine).

An alkylation reaction of this type may be carried out, for example in the manner which has already been described in this application.

Unknown starting materials corresponding to formula II, wherein T represents the group —$NHR_3$ may be obtained, for example by the reaction of a compound II, wherein T represents an alkyl thio group, with an amine $NH_2R_3$ analogously to the instructions of German Offenlegungsschrift No. 2,734,070, page 58, last paragraph to page 59, first paragraph.

For process (b):

The process is carried out, for example in a solvent or dispersing agent at a temperature of from 20° to 180° C., preferably from 40° to 120° C. The following are included as examples of solvents or dispersing agents: aromatic hydrocarbons and chlorohydrocarbons, such as benzene, chlorobenzene, mesitylene, toluene and xylene; saturated cyclic ethers, such as dioxane and tetrahydrofuran; dipolar aprotic solvents, such as dimethylformamide, dimethylacetamide, N-methylpyrrolidone and dimethylsulphoxide or water, and mixtures of these agents.

If Z or U represents an esterified hydroxy group, then this is a reactive ester. A reactive ester is, for example the ester of a strong organic or inorganic acid, such as, in particular of a hydrohalic acid, for example hydrochloric acid, hydrobromic acid or hydriodic acid, or of a sulphonic acid, such as an aryl or alkyl sulphonic acid, in particular lower alkyl sulphonic acid, for example p-toluene sulphonic acid. In the case of an aryl sulphonic acid, phenyl and naphthyl sulphonic acids for example are concerned which are optionally substituted by lower alkyl radicals.

The process is generally carried out in the presence of basic condensing agents, such as alkali hydroxides, strongly basic ion exchangers, alkali alcoholates, such as potassium-tert-butylate or tertiary amines (trialkylamines, for example triethylamine). For example, it is also possible to first of all produce an alkali metal salt from the mercapto compound to be used in liquid ammonia by means of alkali hydrides and to then react this salt with the other reaction component. If Z or U represents a free hydroxy group or the mercapto group, it is advisable to carry out the reaction in a strongly acidic medium, for example in the presence of mineral acids (48% HBr, 6 N—HCl or glacial acetic acid), and it is also possible to use the above-mentioned agents simultaneously as a solvent or dispersing agent.

The reaction may also take place in, for example a two-phase system (for example using chloroform and water) in the presence of a phase transfer catalyst (for example a quaternary ammonium salt, such as benzyl triethyl ammonium chloride) and in the presence of a base (for example sodium hydroxide).

The starting materials corresponding to formula IV may be obtained, for example by the reaction of compounds corresponding to the formula

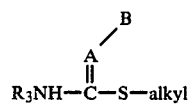

wherein alkyl represents a lower alkyl group, with a compound $H_2N$—$CH_2$—$CH_2$—$Z$, wherein Z represents either a mercapto group or a hydroxy group which is optionally esterified by a strong organic or inorganic acid. This reaction is carried out, for example in solvents, such as lower aliphatic $C_1$–$C_5$ alcohols, acid amides (dimethylacetamine, dimethylformamide) or aromatic hydrocarbons (toluene, xylene), optionally in admixture with water, at a temperature of from 0° to 150° C., preferably from 10° to 120° C. If Z represents a mercapto group, it is advisable to protect this group with a conventional sulphhydryl protective group which may be split off in an acid or base manner. The same protective group, for example are included as sulphhydryl protective groups which are used to protect amino groups, for example the carbobenzoxy group, the carbobenzthio group, the trifluoroacetyl group, the tert.-butyloxycarbonyl group and the like. Moreover, the following S-specific sulphhydryl protective groups are also included by way of example: the 2-nitro-1-phenylethyl group, the benzamidomethyl group, the acetamidomethyl group, the S-ethylmercapto group, the tert.-butyloxycarbonyl sulphenyl group or the benzyloxycarbonylsulphenyl group.

These protective groups are removed at the end of the reaction. This cleavage takes place in a known manner, for example in aqueous, aqueous-alcoholic media or in mixtures of acetone with water and/or alcohols or in pure alcohols in the presence of alkali, such as potassium hydroxide, sodium ethylate, potash or tertiary amines, or secondary or primary amines, these substances preferably being present in equivalent quantities. The protective groups may also be split off in low-molecular weight alcohols with the addition of relatively small quantities of strong acids (hydrochloric acid, sulphuric acid, toluene sulphonic acid, hydrogen bromide/glacial acetic acid). The temperature for splitting off the acyl groups generally ranges from 0° to 150° C. In the case of the benzamidomethyl group or the acetamidomethyl group, the protective groups may also be split off, for example using an aqueous mercury (II) salt solution at room temperature.

The further reaction of the starting materials corresponding to formula IV to produce the products according to the process of the present invention may also take place without these compounds being isolated, simply by directly further reacting the reaction mixture which is obtained according to the reaction described above with a compound corresponding to formula V.

Compounds corresponding to the formula

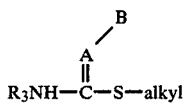

may be obtained, for example by reacting a compound (alkylS)$_2$C=A—B (alkyl=lower alkyl radical) with an amine NH$_2$R$_3$ analogously to the instructions stated in German Offenlegungsschrift No. 2,734,070, page 58, last paragraph to page 59, first paragraph The production of starting materials corresponding to the formula V, wherein U represents a mercapto group or an hydroxy group is stated under process (a).

Starting materials corresponding to formula V, wherein U represents an esterified hydroxy group may be obtained in a conventional manner, for example from the corresponding hydroxy compound by a reaction with conventional halogenation agents (for example thionylchloride, concentrated HCl) or with suitable acid anhydrides (for example acetic acid anhydride). (See German Offenlegungsschrift No. 2,734,070, page 24, paragraph 1, page 37, paragraph 1 and page 64, paragraph 1.) Starting materials corresponding to the formula IV, wherein Z represents an esterified hydroxy group may also be obtained in the same way from the corresponding compounds, in which Z represents the hydroxy group.

For process (c):

This is an alkylation process which is carried out in a known manner. The following are included as examples of alkylating agents: esters corresponding to the formula R'Hal, ArSO$_2$OR' and SO$_2$(OR')$_2$, wherein Hal represents a halogen atom (in particular chlorine, bromine or iodine) and Ar represents an aromatic radical, for example a phenyl or naphthyl radical which may be substituted by one or more lower alkyl radicals, and R' represents an alkyl group which may be substituted, as stated above, having a 1 to 6 or from 1 to 18 carbon atoms, a C$_3$–C$_6$ alkenyl group, a C$_3$–C$_6$ alkinyl group, a C$_6$–C$_8$ bicycloalkyl group, a C$_6$–C$_8$ bicycloalkyl-C$_1$–C$_4$ alkyl group, a C$_6$–C$_{10}$ tricycloalkyl group, a C$_6$–C$_{10}$ tricycloalkyl-C$_1$–C$_4$ alkyl group, a C$_6$–C$_9$ tetracycloalkyl group, a C$_6$–C$_9$ tetracycloalkyl-C$_1$–C$_4$ alkyl group, a phenyl-C$_1$–C$_4$ alkyl group, a C$_3$–C$_{10}$ cycloalkyl group which may be substituted by a C$_1$–C$_6$ alkyl radical, a C$_3$–C$_{10}$-cycloalkyl-C$_1$–C$_4$-alkyl group which may be substituted by C$_1$–C$_6$ alkyl radicals, or an amino-C$_1$–C$_4$ alkyl group, and the latter may also contain a C$_2$–C$_6$ alkanoyl radical or one or two C$_1$–C$_6$ alkyl radicals. Examples include the following: p-toluene-sulphonic acid-C$_1$–C$_{18}$-alkylester, p-toluene-sulphonic acid-(di-C$_1$–C$_4$-alkylamino)C $_{C_1}$–C$_4$-alkylester, C$_1$–C$_{18}$-dialkyl-sulphates, C$_1$–C$_{18}$-alkyl halides, C$_2$–C$_6$-alkenyl halides, C$_3$–C$_6$ alkinyl halides, C$_3$–C$_{10}$-cycloalkyl halides, phenyl-C$_1$–C$_4$-alkyl halides or di-C$_1$–C$_4$-alkylamino-C$_1$–C$_4$-alkyl halides and the like. The alkylation reaction is carried out optionally with the addition of conventional acid-binding agents, such as alkali hydroxides, alkali carbonates or alkali hydrides, at a temperature of from 0° to 150° C. in inert solvents, such as dioxane, dimethylformamide, dimethylsulphoxide, aromatic hydrocarbons (such as benzene and toluene) or acetone. If R$_1$, R$_2$ and R$_3$ represent different substituents, for example if R$_3$ represents a C$_1$–C$_{18}$ alkyl radical and R$_1$ represents a C$_3$–C$_8$ cycloalkyl radical, the alkylation may be carried out in two stages, for example by first of all introducing the alkyl radical and then the cycloalkyl radical, or vice versa. The same applies accordingly if R$_1$ represents, for example a C$_6$–C$_{10}$ tricycloalkyl radical and if R$_2$ represents a C$_1$–C$_6$ alkyl radical. The alkylation may also be carried out in the presence of tetra-alkyl ammonium salts (in particular the halides) combined with alkali hydroxides at a temperature of from 0° to 100° C., preferably from 20° to 80° C., in an aprotic solvent or in chloroform or methylene chloride. The following are included, for example as aprotic solvents: tertiary amides (dimethylformamide, N-methylpyrrolidone, hexamethylphosphoric acid triamide), dimethylsulphoxide, acetonitrile, dimethoxyethane, acetone, and tetrahydrofuran. The last mentioned method is preferably suitable for the alkylation of an —CONH$_2$ group.

If appropriate, the alkylation may also be carried out such that first of all an alkali compound is produced from the compound to be alkylated by reacting it with an alkali metal, alkali hydride or alkali amides (in particular sodium or sodium compounds) at a temperature of from 0° to 150° C. in an inert solvewnt, such as dioxane, dimethylformamide, benzene or toluene, and then adding the alkylating agent.

Instead of using the alkylating agents which have been stated, it is also possible to use other chemically equivalent agents which are conventional in chemistry (see, for example: L. F. and Mary Fieser "Reagents for Organic Synthesis", John Wiley and Sons, Inc., New York, 1967, Vol. 1, pages 1303-4 and Vol. 2, page 471).

The starting materials for this process may be produced according to process (a) using pre-stages in which either the radicals R$_1$, R$_2$ and R$_3$ represent hydrogen or in which one of the radicals R$_1$ or R$_2$ and/or the radical R$_3$ represents hydrogen.

For process (d)

This process is the Mannich reaction and the conditions which are known and are conventional for this reaction are concerned here. The process is preferably carried out, for example under acid conditions (for example in acetic acid) or in an aprotic solvent (for example dichloromethane, dimethylformamide, dimethyacetamide, dimethylsulphoxide or sulpholane) in the presence of an acid (for example acetic acid, HCl). However, the reaction may also be carried out in the absence of acid, and aromatic hydrocarbons (benzene, toluene or xylenes), aliphatic halogenated hydrocarbons (for example dichloromethane or 1,2-dichloroethane) are included by way of example as solvents.

The process is carried out, for example at a temperature of from 0° to 25° C., optionally with cooling. The starting substance $(R_1R_2N)_2CH_2$ may be obtained, for example by reacting 1 mol of formaldehyde (for example aqueous solution) with 2 mols of an amine $R_1R_2NH$ at from 0° to 15° C.

The end materials corresponding to formula I are obtained in a free form or in the form of the salts thereof, depending on the conditions of the process and on the starting materials. The salts of the end substances may be re-converted into the bases in a known manner, for example with alkali or ion exchangers. Salts may be obtained from the bases by a reaction with organic or inorganic acids, in particular with those acids which are suitable for the formation of salts which may be used therapeutically. The following are mentioned as examples of such acids: hydrohalic acids, sulphuric acids, phosphoric acids, nitric acids, perchloric acid, organic mono-, di- or tricarboxylic acids of the aliphatic, alicyclic, aromatic or heterocyclic series, and sulphonic acids. Examples of these are as follows: formic acid, acetic acid, propionic acid, succinic acid, glycolic acid, lactic acid, malic acid, tartaric acid, citric acid, ascorbic acid, maleic acid, fumaric acid, hydroxymaleic acid or pyroracemic acid; phenylacetic acid, benzoic acid, p-aminosalicylic acid, embonic acid, methane sulphonic acid, ethane sulphonic acid, hydroxyethane sulphonic acid, ethylene sulphonic acid; halogenbenzene sulphonic acid, toluene sulphonic acid, naphthalene sulphonic acid or sulphanilic acid, or 8-chloro-theophylline.

In the above-mentioned processes for the production of the compounds according to the present invention, amino groups which are present in the starting substances and which do not take part in the reaction may contain known and conventional protective groups. These are in particular radicals which are readily cleavable by hydrolysis or hydrogenolysis and are optionally already split off during the reaction. If such protective groups are not split off during the reaction of the process, then this occurs after the reaction. The starting compounds often already contain such protective groups due to their production.

These protective groups are, for example readily solvolytically cleavable acyl groups or readily hydrogenolytically cleavable groups. The solvolytically cleavable protective groups are split off, for example by saponification with dilute acids or by means of basic substances (potash, soda, aqueous alkali solutions, alcoholic alkali solutions, aqueous $NH_3$) at a temperature of from 10° to 150° C., in particular from 20° to 100° C. Hydrogenolytically cleavable groups, such as α-arylalkyl radicals (benzyl radical) or aralkoxy carbonyl radicals (carbobenzoxy radical) are appropriately split off by catalytic hydrogenation in the presence of conventional hydrogenation catalysts, in particular palladium catalysts, platinum oxide or Raney nickel, in a solvent or dispersing agent, optionally under elevated pressure at a temperature of from 20° to 100° C., in particular from 40° to 80° C. The following are included by way of example as solvents or dispersing agents: water, lower aliphatic alcohols, cyclic ethers, such as dioxane or tetrahydrofuran, aliphatic ethers, dimethylformamide, etc., as well as mixtures of these agents.

The following are included as examples of protective groups which may be split off by hydrogenolysis: the benzyl radical, the α-phenyl ethyl radical, benzyl radicals substituted in the benzene nucleus (p-bromo- or p-nitrobenzyl radical) the carbobenzoxy radical and the carbobenzthio radical. Examples of hydrolytically cleavable radicals include the following: the trifluoroacetyl radical, the phthalyl radical, the tirtyl radical, the p-toluenesulphonyl radical and the like, as well as lower alkanoyl radicals, such as the acetyl radical, the formyl radical, the tert.-butyloxycarbonyl radical and the like.

The protective groups which are conventional in peptide synthesis and the cleavage processes which are conventional in this respect are concerned in particular. Reference is made, inter alia, to the book by Jesse P. Greenstein and Milton Winitz entitled "Chemistry of Amino Acids", N.Y., 1961, John Wiley & Sons, Inc., Volume 2, for example page 883 et seq.). The carbalkoxy group (for example, low molecular weight) is also included.

If the starting materials also contain hydroxy groups, mercapto groups and/or primary amino groups, these may also be protected by the protective groups which are mentioned above and were also mentioned earlier on, cleavage taking place in the same manner.

Those compounds corresponding to formula I which contain asymmetric carbon atoms and are usually produced as racemates may be split into the optically active isomers in a known manner, for example by means of an optically active acid or by chromatographic resolution (see, for example Angewandte Chemie 92/1 (1980), page 14). However, it is also possible to use an optically active starting substance from the beginning, in which case a corresponding optically active or diastereomeric form is then obtained as the end product.

Thus, the present invention also includes the D- and L-forms, as well as the DL mixture in the event that an asymmetric carbon atom occurs in the compound corresponding to formula I and in the event of two and more asymmetric carbon atoms, likewise the corresponding diastereomeric forms.

The compounds corresponding to formula I may also be present in corresponding tautomeric forms (if A represents a nitrogen atom), in which case they may then be present completely or partly in one of the possible tautomeric forms. An equilibrium generally prevails under the normal working and storage conditions. This invention relates to all tautomeric forms and to all diastereoisomers and optical enantiomers of the compounds according to formula I.

Pharmacological and pharmaceutical data

The compounds according to this invention are suitable for the preparation of pharmaceutical compositions and preparations. the pharmaceutical compositions or medicaments contain as active principle one or more of the compounds according to the invention, optionally in admixture with other pharmacologically or pharmaceutically active substances. The medicaments are prepared in known manner with the usual pharmaceutical additives and other conventional excipients and diluents.

Examples of excipients and additives of this kind are the substances recommended and specified in the following literature references as additives for pharmacy, cosmetics and related fields: Ullmanns Encyklopadie der technischen Chemie, Vol. 4 (1953), pages 1 to 39; Journal of Pharmaceutical Sciences, Vol. 52 (1963), pages 918 et seq., H.v.Czetsch-Lindenwald, Hilfsstoffe fur Pharmazie und angrenzende Gebiete; Pharm. Ind., No. 2, 1961, pages 72 et seq.; Dr. H. P. Fiedler, Lexikon der Hilfsstoffe fur Pharmazie, Kosmetik und angrenzende Gebiete Cantor KG. Aulendorf (Wurtt.) 1971.

Examples of such materials include gelatin, natural sugars such as sucrose or lactose, lecithin, pectin, starch (for example cornstarch), alginic acid, tylose, talc, lycopodium, silica (for example collodial silica), glucose, cellulose, cellulose derivatives, for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methyl stearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially medium viscosity dimethyl polysiloxane), magnesium carbonate and the like.

For the production of solutions, there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., glyceryl monostearate, glyceryl distearate, glyceryl monopalmitate, paraffins, and the like.

In the production of the composition, there can be used known and customary solution aids or emulsifiers. As solution aids and emulsifiers, there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyoleotriglycerides, linolized oleotriglycerides, polyethylene oxide-condensation products of fatty alcohols, alkylphenols or fatty acids or also 1-methyl-3-(2-hydroxyethyl)-imidazolidone-2. As used herein, polyoxyethylated means that the materials in question contain polyoxyethylene chains whose degree of polymerization generally is between 2 and 40, particularly between 10 and 20.

Such polyoxyethylated materials, for example, can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives, stabilizers, buffers, for example, calcium hydrogen phosphate, collodial aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred a neutral to weak acid (to pH 5) pH value.

As antioxidants, there can be used, for example, sodium meta bisulfite, ascorbic acid, gallic acid, alkyl gallates, e.g., methyl gallate and ethyl gallate, butyl hydroxyanisole, nordihydroguaratetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmacological and galenical treatment of the compounds of the invention is carried out according to the usual standard methods. For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides, reference is made to the following standard textbook: Sucker, Fuchs, Speiser, Pharmazeutische Technologie, Thieme-Verlag, Stutgart, 1978.

The active principles or medicaments may be applied to the skin or mucosa or into the interior of the body, for example orally, enterally, pulmonarily, rectally, nasally, vaginally, lingually, intravenously, intra-arterially, intracardially, intramuscularly, intraperitoneally, intracutaneously or subcutaneously.

In particular, the addition of other active medicaments is also possible and favorable.

The compounds according to the present invention exhibit, for example an effective stomach acid-secretion inhibiting and anti-ulceration effect and a specific stomach-spasmolytic effect.

The stomach acid-secretion inhibiting effect may be determined, for example using the following experimental models:

(a) Model of perfused rat stomach lumen with pentagastrin or histamine stimulation according to M. N. Ghosh and H. O. Schild, Brit. J. Pharmacol. 13 (1958), pages 54–61, and Rosenoer and Schild, the assay of urogastrone J. Physiol. 162 (1962), page 155. The method was modified in that before the beginning of stimulation, the stomach of the rat was not cut open to remove remnants of food, but was only rinsed through with warm common salt solution (0.9%). The test substances are applied intravenously or intraduodenally.

(b) Model of conscious chronic fistulated cat with histamine stimulation (according to Makowitz, Experimental Surgery, 3rd edition, 1954, page 200 et seq., Williams and Wilkins Company). The test substances are applied intravenously or intragastrally.

(c) Model of the Shay cat (pylorus ligation according to Shay, II. et al.: Gastroenterology 5, 43–61, 1945). The test substances are applied perorally.

(d) Model of the Heidenhain-pouch-fistulated dog with pentagastrin or histamine stimulation. (Journal of Surgical Research 7 (1967), page 383 et seq., Heidenhain, R.: Fluger's Archiv ges. Physiol. 18, 169 (1878). The test substances are applied intravenously or intragastrally.

The anti-ulcerative effect may be demonstrated, for example on an ulcer which is produced by artificial means in a rat. For example, the ulcer is caused using a combination of cold stress and the antiphlogistic "Indometacin". The test method is carried out according to Levin, R. J., Peptic Ulcer, published by C. J. Pfeiffer Munksgaard, Kopenhagen, pages 92–97 (1971) and Jahn, Adrian, Arzneimittel Forschung (Drug Research) Vo. 19 (1969), pages 36–52, and the following modifications are made. After the "Indometacin" has been applied, the animals are kept for 3 hours in immobilization cages in a refrigerator at from 4° to 5° C. Moreover, the test substances are administered perorally one hour before the indometacin is applied.

The stomach-spasmolytic effect may be demonstrated, for example on the model of the carbachol spasm of the rat stomach according to the method of Zwage Makers, J.M.A., V. Classen, Arzneimittel-Forschung (Drug Research) 30, 1517, 1980. The test substances are applied intraduodenally. In this model, the stomach-spasmolytic effect of the compound according to Example 1 is, for example 3.8 times greater than that of "Ranitidin".

For example, a 50% inhibition of the stomach acid secretion is established on the model of the perfused rat stomach lumen with pentagastrin stimulation, in the case of an intravenous dose of 0.088 mg/kg body weight/rat. This stomach acid-secretion inhibiting effect is comparable with the effect of the known medicament "Ranitidin".

The lowest effective dose in the last-mentioned animal experiment is, for example:

0.05 mg/kg intravenous (in the model of the perfused rat stomach lumen with pentagastrin stimulation).

The general dose range for the stomach acid-secretion inhibiting effect in the animal experiment (perfused rat stomach lumen) is, for example from 1 to 100 mg/kg and more particularly from 1 to 20 mg/kg (oral) of from 0.05 to 20 mg/kg and more particularly from 0.05 to 5 mg/kg (intravenous).

Indications for which the compounds according to the present invention may be used include acute or chronic gastritis, nervous irritable stomach, hyperacidity of the gastric juice, *Ulcus ventriculi et duodeni*.

The pharmaceutical preparations generally contain from 1 to 2,000 mg and preferably from 2 to 300 mg of the active component(s) according to the present invention.

The preparations may be administered, for example in the form of tablets, capsules, pills, dragees, suppositories, ointments, jellies, creams, powdeers, dusting powders, aerosols or in liquid form. Examples of liquid formulations are oily or alcoholic or aqueous solutions, suspensions and emulsions. Preferred formulations are tablets containing from 5 to 100 mg of active substance, or solutions containing from 0.1 to 20% of active substance.

The active components according to the present invention may be used in individual doses of, for example:

(a) from 2 to 2,000 mg, preferably from 10 to 200 mg in the case of oral formulations, (b) from 2 to 2,000 mg, preferably from 5 to 50 mg in the case of parenteral formulations (for example intravenous, intramuscular), (c) from 2 to 2,000 mg, preferably from 10 to 200 mg in the case of formulations for rectal application (these doses being based on the free base in each case).

For example, 1 to 3 tablets containing from 1 to 400 mg of active substance may be prescribed three times daily or, for example in the case of intravenous injection, one 1 to 2 ml ampoule containing a from 1 to 200 mg of active substance may be prescribed one to three times daily. In the case of oral administration, the minimum daily dose is, for example 10 mg, while the maximum daily dose should not exceed 2,000 mg.

The acute toxicity of the compounds according to the present invention in mice (expressed by the LD 50 mg/kg method: probite analysis according to Cavalli-Sforza, in: Biometrie, Gustav Fischer-Verlag, Stuttgart, 1974), is above 100 mg/kg in the case of, for example oral application. For some compounds, the LD 50 is above 800 mg/kg.

The medicaments may be used in human medicine either individually or in admixture with other pharmacologically active substances.

Unless otherwise indicated, all parts and percentages are by weight.

The compositions can comprise, consist essentially of, or consist of the materials set forth.

The methods can comprise, consist essentially of, or consist of the steps set forth with the materials shown.

EXAMPLE 1

N-[2-[[5-(tricyclo(2.2.1.0$^{2.6}$)hept-3-yl-amino-methyl)-2-furanyl]-methylthio]-ethyl]-N'-methyl-2-nitro-1,1-ethylene-diamine

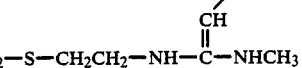

A suspension of 37.2 g of N-[2-[[5-(tricyclo(2.2.1.0$^{2.6}$)hept-3-yl-amino-methyl)-2-furanyl]-methylthio]-ethyl]-1-methylthio-2-nitro-1,1-ethylene-diamine in 1 litre of ethanol is mixed with 50 ml of methylamine with stirring and cooling with ice, and is stirred for 4 hours at 0° C. until a clear solution is produced. The mixture is the concentrated under vacuum at room temperature and the remaining residue is dried under a high vacuum at 40° C.

Yield: 38.5 g.
R$_f$: 0.26 (eluant: chloroform:methanol:concentrated ammonia 90:10:1).

Hydrochloride

A solution, prepared at 45° C., of 38.5 g of base in 280 ml of ethanol is mixed with 23.2 ml of 4.36 N ethereal hydrochloric acid with stirring and cooling with ice. The hydrochloride is stored over night at 0° C. to complete the precipitation. It is then suction filtered, washed with pre-cooled ethanol and dried under vacuum. Recrystallization is carried out in a solvent mixture of ethanol and methanol (3:2).

Yield: 31.1 g.
M.P. 174° C.

Production of the starting materials (a) 5-tricyclo(2.2.1.0$^{2.6}$)hept-3-yl-aminomethyl)-(2-furanyl)-methanol A solution, heated to about 40° C. under a supply of nitrogen, of 96 g of tricyclo(2.2.1.0$^{2.6}$) hept-3-ylamine-hydrochloride (Chemische Berichte 98, page 109 (1965) and 64.7 g of (2-furanylmethanol in 580 ml of ethanol is mixed with 30 g of paragormaldehyde and heated for 3 hours at 70° C. 10.2 g of paraformaldehyde are added to complete the reaction and the mixture is also heated for 4 hours at 70° C. Thereafter, it is concentrated under vaccuum, the residue is dried under vacuum at 40° C. until it is free of solvent and is then dissolved in 450 ml of water. The solution is adjusted to pH 6–7 and is extracted three times with ether to remove the excess 2-furanylmethanol. The aqueous phase is adjusted to pH 10–11 using 32% sodium hydroxide sulphate, filtered and concentrated under vacuum. The residue is purified in an ethanolic solution with active carbon and silica gel, filtered, concentrated under vacuum and the product obtained thus is dried at 40° C.

Yield: 94.5 g.
R$_f$: 0.47 (eluant: chloroform:methanol:concentrated ammonia 90:10:1).

(b) 2-[[5-(tricyclo(2.2.1.0$^{2.6}$)hept-3-yl-aminomethyl)-2-furanyl]-methylthio]-ethane amine. A solution, prepared while cooling with ice, of 94.59 g of 5-(tricyclo(2.2.1.0$^{2.6}$)hept-3-yl-amino)-methyl)-(2-furanyl)-methanol in about 200 ml of concentrated hydrochloric acid is mixed dropwise at from 0° to 5° C. and with stirring with a solution of 49 g of cysteaminehydrochloride in 200 ml of concentrated hydrochloric acid. The mixture is stirred for one and half hours in an ice bath, then neutralized with sodium carbonate while cooling with ice, and thereafter adjusted to be alkaline with 32% sodium hydroxide. The aqueous, alkaline solution is extracted four times with, in each case, 150 ml of n-butanol, and the combined butanol extracts are dried with anhydrous sodium sulphate. After filtration and concentration of the filtrate under vacuum, an oily residue is produced which is purified in an acid-alkaline manner and is finally treated with active carbon and silica gel in an ethanolic solution, and the desired compound is produced in a pure form.

Yield: 72 g.
R$_f$: 0.43 (eluant: chloroform:methanol: concentrated ammonia 85:15:1).

(c) N-[2-[[5-tricyclo(2.2.1.0$^{2.6}$)hept-3-yl-aminomethyl)-2-furanyl]-methylthio]-ethyl]-1-(methylthio)-2-nitro-ethylene amine.

A solution of 50 g of 2-[[5-(tricyclo(2.2.1.0$^{2.6}$)hept-3-yl-amino-methyl)-2-furanyl]-methylthio]-ethane amine in one liter of isopropanol is mixed with 38.6 g of 1-nitro-2,2-bis-(methylmercapto)-ethylene with stirring, and the solution is heated for three and a half hours at 70° C. The methylmercaptan which forms during the reaction is passed into an aqueous sodium hypochlorite solution in a stream of nitrogen. The reaction solution is then concentrated under vacuum, the residue is dried intensively at 30° C. under a high vacuum and is purified in an ethanolic solution over active carbon and silica gel. The solution is filtered, re-concentrated under vacuum, and the remaining residue is recrystallized from isopropanol. The crystalline deposit is suction filtered, washed with ice-cooled isopropanol and dried at 40° C., thus producing a compound which in uniform according to thin layer chromatography.

Yield 47.4 g.
M.p. 94° C.
(Eluant: chloroform:methanol:concentrated ammonia 90:10:1).

EXAMPLE 2

N-[2-[[5-tricyclo(2.2.1.0$^{2.6}$)hept-3-yl-amino-methyl)-2-furanyl]-methylthio]-ethyl]-N'-(n-octyl)-2-nitro-1,1-ethylene-diamine.

The formula is the same as for Example 1 except that R$_3$ represents the radical —(CH$_2$)$_7$—CH$_3$.

A suspension of 4 g of N-[2-[[5-(tricyclo(2.2.1.0$^{2.6}$)hept-3-yl-amino-methyl)-2-furanyl]-methylthio]-ethyl]-1-(methylthio)-2-nitroethene amine in 50 ml of ethanol is mixed with a solution of 2.58 of noctyl-amine in 8 ml of ethanol. The reaction solution is heated for eight and a half hours at 60° C. under a supply of nitrogen, is cocnentrated under vacuum and the remaining residue is purified over a silica (eluant:chloroform:methanol 9:1). The desired compound which is uniform according to thin layer chromatogrphy crystallizes after standing for several hours at 0° C. and the crystals are dried at 40° C. under a high vacuum (eluant: chloroform:methanol 9:1).

Yield: 2.2 g.
M.p. 70°–71° C.

EXAMPLE 3

N-[2-[[5-tricyclo(2.2.1.0$^{2.6}$)hept-3-yl-amino-methyl)-2-furanyl]-methylthio]-ethyl]-N'-allyl-2-nitro-1,1-ethylene-diamine.

The formula is the same as for Example 1 except tha R$_3$ represents the radical —CH$_2$—CH=CH$_2$.

A suspension of 4 g of N-[2-[[5-tricyclo(2.2.1.0$^{2.6}$)hept-3-yl-amino-methyl)-2-furanyl]-methylthio]-ethyl]-1-(methylthio)-2-nitroethylene amine in 50 ml of ethanol is mixed with stirring with a solution of 1.14 g of allylamine in 5 ml of ethanol. The reaction solution is heated for 9 hours at from 50° to 60° C. under a supply of nitrogen, is then concentrated under vacuum at 40° C., resteamed several times with ethanol and, finally the residue is purified in an ethanolic solution with active carbon and silica gel. Filtration and concentration of the solution under vacuum results in a residue which crystallizes after triturating with ether. The product is filtered and then washed with ether. The compound is uniform according to thin layer chromatogrhpy (eluant:chloroform:methanol 9:1).

Yield: 2.9 g.
M.p. 74° C.

EXAMPLE 4

N-[2-[[5-(tricyclo(2.2.1.0$^{2.6}$)hept-3-yl-amino-methyl)-2-furanyl]-methylthio]-ethyl]-N'-prop-1-inyl-2-nitro-1,1-ethylene-diamine The formula is the same as for Example 1 except that R$_3$ represents the radical —CH—C≡CH.

A solution of 5 g of N-[2-[[5-(tricyclo(2.2.1.0$^{2.6}$)hept-3-yl-amino-methyl)-2-furanyl]-methylthio]-ethyl]-1-(methylthio)-2-nitroethylene amine in 60 ml of methanol is mixed with 1.39 g of 3-aminoprop-1-ine and heated for 2 to 3 hours at 40° C. with stirring and under a supply of nitrogen. The reaction solution is concentrated under vacuum, purified in an ethanolic solution with active carbon, filtered, the solvent is removed under vacuum and the solution is resteamed several times with ethanol. The remaining residue crystallizes at 0° C. The crystallized material is then recrystallized from a little ethanol.

Yield: 3.2 g.
M.p. 110° C.

EXAMPLE 5

N-[2-[[5-(tricyclo(2.2.1.0$^{2.6}$)hept-3-yl-amino-methyl)-2-furanyl]-methylthio]-ethyl]-N'-(2-methoxy-ethyl)-2-nitro-1,1-ethylene-diamine.

The formula is the same as for Example 1 except that R$_3$ represents the radical —CH$_2$—CH$_2$—OCH$_3$.

A suspension of 4 g of N-[2-[[5-(tricyclo(2.2.1.0$^{2.6}$)hept-3-yl-amino-methyl)-2-furanyl]-methylthio]-ethyl]-1-(methylthio)-2-nitroethylene amine in 50 ml of ethanol is mixed with a solution of 1.51 g of 2-methoxyethylamine in 5 ml of ethanol. The reaction solution is heated for 5 hours at 60° C. under a nitrogen atmosphere, is then concentrated under vacuum, resteamed several times with ethanol and the residue is purified over a silica (eluant: chloroform:methanol 9:1)

Yield: 4.9 g.
R$_F$: 0.46 (eluant: chloroform:methanol 9:1).

EXAMPLE 6

N-[2-[[5-(tricyclo(2.2.1.0$^{2.6}$)hept-3-yl-amino-methyl)-2-furanyl]-methylthio]-ethyl]-N'-cyclopropyl-2-nitro-1,1-ethylene-diamine.

The formula is the same as for Example 1 except that R$_3$ represents the cyclopropyl radical.

A solution of 3.07 of N-[2-[[5-(tricyclo(2.2.1.0$^{2.6}$)hept-3-yl-amino-methyl)-2-furanyl] -methylthio]-ethyl]-1-(methylthio)-2-nitroethylene amine in 30 ml of ethanol is mixed with a solution of 0.443 g of cyclopropylamine in 5 ml of ethanol. The reaction solution is heated for four and a half hours at 40° C. under a supply of nitrogen, a solution of 0.22 g of cyclopropylamine in 3 ml of ethanol is then added and the mixture is heated for a further 8 hours at 40° C. The solution is concentrated under vacuum, resteamed several times with ethanol, purified in an ethanolic solution with active carbon, filtered and re-concentrated under vacuum. The remaining residue is purified over a silica gel column (eluant: chloroform:methanol: 9:1). The compound is uniform according to thin layer chromatography.

Yield: 1.8 g.
R$_f$: 0.34 (eluant: chloroform:methanol 9:1).

EXAMPLE 7

N-[2-[[5-(tricyclo(2.2.1.0$^{2.6}$)hept-3-yl-N-methyl-amino-methyl)-2-furanyl]-methylthio]-ethyl]-N'-methyl-2-nitro-1,1-ethylene diamine.

The formula is the same as for Example 1 except that R$_2$ represents a methyl group.

A solution of 6.24 g of N-[2-[[5-(tricyclo(2.2.1.0$^{2.6}$)hept-3-yl-N-methyl-aminomethyl)-2-furanyl]-methylthio]-ethyl]-1-(methylthio)-2-nitroethylene amine in 100 ml of ethanol is mixed with 10 ml of methylamine. The reaction solution is stirred for 1 hour at 0° C. and then the temperature of the solution is allowed to slowly rise to 20° C. and the solution is then concentrated under vacuum at 40° C. The remaining residue is purified over a silica gel column by chromatography (eluant: chloroform: methanol: concentrated ammonia 92:7:1). The compound which has crystallized by triturating with ether is dried at 40° C. under a high vacuum.

Yield: 4.9 g.
R$_f$: 0.32 (eluant: chloroform:methanol:concentrated ammonia 90:10:1).

EXAMPLE 8

N-[2-[[5-(tricyclo(3.3.1.0$^{3.7}$)dec-1-yl-amino-methyl)-2-furanyl]-methylthio]-ethyl]-N'-methyl-2-nitro-1,1-ethylene diamine.

The formula is the same as in Example 1 except that R$_1$ represents a tricyclodecyl radical as mentioned earlier.

A solution, cooled to 0° C., of 5g of N-[2-[[5-(tricyclo(3.3.1.1$^{3.7}$)dec-1-yl-amino-methyl)-2-furanyl]-methylthio]-ethyl]-1-(methylthio)-2-nitroethylene amine in 70 ml of absolute ethanol is mixed with 3.5 ml of methyl amine, and the reaction solution is stirred for 2 hours at 0° C. A further 5 ml of methyl amine are then added and the solution is again stirred for 5 hours at 0° C. The reaction solution is then concentrated under vacuum, resteamed several times with ethanol and purified by column chromatography (eluant: chloroform::methanol: concentrated ammonia 90:10:1). The compound is obtained in a cyrstalline form which is uniform according to thin layer chromatography (eluant: chloroform:methanol: concentrated ammonia 90:10:1).

Yield: 3.8 g.
M.p. 55°–57° C.

Production of the starting materials
(a) 5-[(tricyclo(3.3.1.1$^{3.7}$)dec-1-yl-amino)-methyl]-2-furanyl-methanol

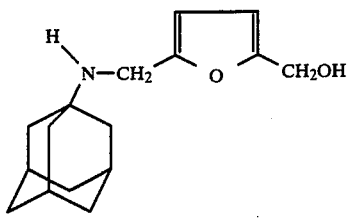

A solution heated to about 40° C. under a supply of nitrogen, of 30 g of 1-amino-adamantanehydrochloride and 15.7 g of 2-furanyl-methanol in 140 ml of absolute ethanol is mixed with 7.2 g of paraformaldehyde and heated for 15 hours at 70° C. (2.4 g of paraformaldehyde are added after 5 hours and 7.8 g of 2-furanylmethanol are added after 9 hours to complete the reaction). The solution is concentrated under vacuum after 15 hours and the remaining residue is dissolved in 100 ml of water and adjusted to pH 2 with 2 N hydrochloric acid. The aqueous phase which contains hydrochloric acid is extracted three times with ether, the aqueous solution is alkalized with sodium hydroxide to pH 10 and is extracted four times with n-butanol. The butanol extracts are dried with anhydrous sodium sulphate, filtered and concentrated under vacuum. The residue is purified in an ethanolic solution with active carbon and silica gel, filtered, concentrated under vacuum, and dried at 40° C.

Yield: 21 g.

$R_F$: 0.52 (eluant: chloroform:methanol: concentrated ammonia 90:10:1).

(b) 2-[[5-(tricyclo(3.3.1.1$^{3.7}$)dec-1-yl-aminomethyl)-2-furanyl]-methylthio]-ethane amine A solution, prepared while cooling with ice, of 17.7 g of 5-[(tricyclo(3.3.1.1$^{3.7}$)dec-1-yl-aminomethyl-2-furanyl]-methanol in 44 ml of concentrated hydrochloric acid is mixed dropwise with a solution of 7.8 g of cysteamine-hydrochloride in 11 ml of concentrated hydrochloric acid with stirring at from 0° to 5° C. The mixture is stirred for 2 hours at 0° C., neutralized with sodium carbonate while cooling with ice and thereafter the solution is adjusted to pH 14 with 32% sodium hydroxide. The aqueous, alkaline solution is extracted four times with butanol. the butanol extracts are combined and washed with anhydrous sodium sulphate, filtered and concentrated under vacuum. Finally, the remaining residue is purified in an ethanolic solution with active carbon and silica gel, and the desired compound is then obtained in a homogeneous form.

Yield: 18.5 g.

$R_f$: 0.45 (eluant: chloroform:methanol: concentrated ammonia 85:15:1).

(c) N-[2-[[5-(tricyclo(3.3.1.1$^{3.7}$)dec-1-yl-aminomethyl)-2-furanyl]-methylthio]-ethyl-1-(methylthio)-2-nitro-ethylene amine.

A solution of 17.5 g of 2-[[5-(tricyclo(3.3.1.1$^{3.7}$)dec-1-yl-amino-methyl)-2-furanyl]-methylthio]-ethane amine in 140 ml isopropanol is mixed with 9 g of 1-nitro-2,2-bis-methyl-mercapto-ethylene with stirring, and the solution is heated for three and a half hours at 70° C. under a supply of nitrogen. The methylmercaptan which forms during the reaction is passed into an aqueous sodium hypochlorite solution in a stream of nitrogen. The reaction solution is then concentrated under vacuum, the residue is dried intensively under a high vacuum at 30° C., purified in an ethanolic solution over active carbon and silica gel, the solution is filtered, re-concentrated under vacuum and the remaining residue is recrystallized from isopropanol.

Yield: 16 g.
M.p. 92° C.

EXAMPLE 9

N''-cyano-N-methyl-N'-[2-[5-[tricyclo (2.2.1.0$^{2.6}$)hept-3-yl-amino-methyl)-2-furanyl]methyl-thio]ethyl]-guanidine

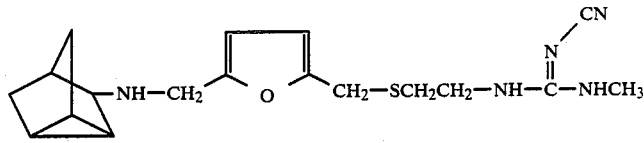

12.7 g (0.1 mol) of N-methyl-O-ethyl-N'-cyano-isourea are suspended in 200 ml of water and heated for 30.6 g (0.11 mols) of 2-[[5-tricyclo(2.2.1.0$^{2.6}$)hept-3-yl-amino-methyl)-2-furanyl]-methylthio]-ethane amine in 250 ml of 20% ethanol. The mixture is then concentrated under vacuum and the remaining residue is purified over a silica gel column (eluant: chloroform:methanol: concentrated ammonia=90:10:1).

Yield: 26.3 g.

$R_F$: 0.54 (eluant: chloroform:methanol: concentrated ammonia 90:10:1).

The compound may also be produced using a compound corresponding to formula III, wherein V represents the group—NHR$_2$ (here—NHCH$_3$): 7.31 g of N-cyano-N'[[5-(tricyclo(2.2.1.0$^{2.6}$)hept-3-yl-amino-methyl)-2-furanyl]-methylthio]-ethyl]-S-methyl-isothiourea are dissolved in 150 ml of ethanol and mixed with 20 ml of methylamine. The reaction solution is then stirred for 1 hour in an ice bath, then concentrated under vacuum at 40° C., and the remaining residue is purified over a silica gel column (eluant: chloroform-:methanol: concentrated ammonia=90:10:1).

Yield: 4.9 g.

$R_F$: 0.53 (eluant: chloroform:methanol:concentrated ammonia 90:10:1).

EXAMPLES OF PHARMACEUTICAL PREPARATION

Example: Capsules 12 kg of the compound according to Example 1 (as hydrochloride) are granulated in a known manner with a solution of 0.25 kg of gelatin in 2.25 kg of water in a fluidized bed spray granulation apparatus. 0.8 kg of cornstarch, 0.1 kg of magnesium stearate and 0.05 kg of highly dispersed silicon dioxide are added, and the mixture is charged in a quantity of 330 mg in each case into hard gelatin capsules of size zero. One capsule contains 300 mg of the active substance in the form of hydrochloride.

EXAMPLE: INJECTION SOLUTION 54.8 g of the compound according to Example 1 (as hydrochloride) and 10.285 g of sodium chloride are dissolved successively in 1.5 liters of water for injection purposes. The solution is made up to 2 liters with water for injecting and, after mixing, is filtered in a sterile manner through a membrane filter which has a suitable mesh width. Thereafter, the solution is charged into 2 ml sterilized ampoules under aseptic conditions. One ampoule contains 54.8 mg of the active substance in the form of hydrochloride.

The entire disclosure German priority application P 3245387.6 is hereby incorporated by reference.

We claim:

1. A compound corresponding to the formula

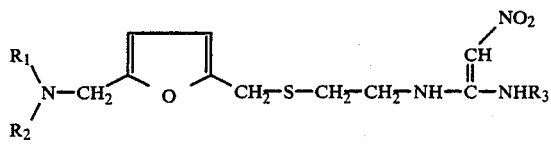

wherein
R$_1$ represents a C$_6$–C$_{10}$-tricycloalkyl group,
R$_2$ represents hydrogen or a C$_1$–C$_6$ alkyl group and represents hydrogen, C$_1$–C$_{10}$-alkyl- group, a C$_3$–C$_6$-cycloalkyl group, a C$_3$–C$_6$-alkenyl group, a C$_3$–C$_6$-alkenyl group or a C$_1$–C$_4$-alkoxy-C$_1$–C$_6$-alkyl group.

2. A compound according to claim 1 wherein R$_1$ is a C$_6$–C$_{10}$-tricycloalkyl group, R$_2$ is hydrogen or a C$_1$–C$_4$-alkyl group, R$_3$ is a C$_1$–C$_{10}$-alkyl group, a C$_3$–C$_4$-alkinyl group, a C$_3$–C$_6$-cycloalkyl group or a C$_1$–C$_6$-alkyl group which is substituted by a C$_1$–C$_4$ alkoxy group.

3. A medicament comprising a compound of formula I according to claim 1 in an amount effective to have pharmacological activity.

4. A medicament according to claim 3 having the ability to inhibit secretion of gastric juice or having an H$_2$-blocker type antihistamine effect, or an ulcer curing or inhibiting effect, or a stomach-spasmolytic effect.

5. A composition according to claim 4 containing 1 to 2000 mg of the compound of formula I.

6. A method of inhibiting secretion of gastric juice comprising administering to a mammal a compound of formula I according to claim 1 in an amount effective to inhibit said secretion.

7. A method of imparting an H$_2$-blocker type antihistamine effect comprising administering to a mammal a compound of formula I of claim 1 in an amount effective for the antihistamine effect.

8. A method of curing ulcers of inhibiting the development of ulcers comprising administering to a mammal a compound of formula I of claim 1 in an amount effective for the ulcer curing or inhibiting effect.

9. A method of imparting a stomach-spasmolytic effect comprising administering to a mammal a compound of formula I of claim 1 in an amount effective for the stomach-spasmolytic effect.

10. A compound according to claim 1 which is N-[2-[[5-(tricyclo (2.2.1.0$^{2.6}$)hept-3-yl-amino-methyl)-2-furanyl[-methylthio[ethyl[-N$^1$-methyl-2-nitro-1,1-ethylene-diamine or a salt thereof.

11. A medicament comprising a compound according to claim 10 in an amount effective to have pharmacological activity.

12. A medicament according to claim 11 having the ability to inhibit secretion of gastric juice or having an H$_2$-blocker type antihistamine effect, or an ulcer curing or inhibiting effect, or a stomach-spasmolytic effect.

13. A medicament according to claim 4 containing 1 to 2000 mg of said compound.

14. A method of inhibiting secretion of gastric juice comprising administering to a mammal a compound according to claim 10 in an amount effective to inhibit said secretion.

15. A method of imparting a H$_2$-blocker type antihistamine effect comprising administering to a mammal a compound of claim 10 in an amount effective for the antihistamine effect.

16. A method of curing ulcers or inhibiting the development of ulcers comprising administering to a mammal a compound of claim 10 in an amount effective for the ulcer curing or inhibiting effect.

17. A method of imparting a stomach-spasmolytic effect comprising administering to a mammal a compound of claim 10 in an amount effective for the stomach-spasmolytic effect.

18. A compound according to claim 1 where R$_1$ is a tricycloheptyl group, R$_2$ is hydrogen or methyl, R$_3$ is hydrogen, C$_1$ to C$_6$ alkyl, propin-(b 3)-yl-1-, cyclopropyl or methoxyethyl.

19. A compound according to claim 18 where R$_3$ is hydrogen or a C$_1$ to C$_6$ alkyl.

* * * * *